(12) United States Patent
Chen et al.

(10) Patent No.: US 7,544,783 B2
(45) Date of Patent: Jun. 9, 2009

(54) FUSION PROTEIN FOR TREATMENT OF ALLERGIC DISEASES

(75) Inventors: Haiming Chen, Los Angeles, CA (US); Junyu Gao, Beijing (CN)

(73) Assignees: Xianggui Wu, Hacienda Heights, CA (US); Jun Bao, Hacienda Heights, CA (US)

( * ) Notice: Subject to any disclaimer, the term of this patent is extended or adjusted under 35 U.S.C. 154(b) by 0 days.

(21) Appl. No.: 10/592,376

(22) PCT Filed: May 8, 2004

(86) PCT No.: PCT/CN2004/000449

§ 371 (c)(1),
(2), (4) Date: Nov. 30, 2006

(87) PCT Pub. No.: WO2005/085291

PCT Pub. Date: Sep. 15, 2005

(65) Prior Publication Data

US 2008/0015347 A1    Jan. 17, 2008

(30) Foreign Application Priority Data

Mar. 10, 2004    (CN) ........................ 2004 1 0006498

(51) Int. Cl.
*C12P 21/08*    (2006.01)

(52) U.S. Cl. .............. 530/387.3; 424/133.1; 424/185.1; 424/192.1; 530/388.22; 530/862; 530/868

(58) Field of Classification Search ....................... None
See application file for complete search history.

(56) References Cited

U.S. PATENT DOCUMENTS 7,265,208 B2 *   9/2007   Saxon et al. ............. 530/387.1
2003/0082190 A1 *   5/2003   Saxon et al. ............. 424/178.1

FOREIGN PATENT DOCUMENTS

WO    WO 02/088317    *   9/2002
WO    WO 02/088317 A2   11/2002
WO    WO 02/102320 A2   12/2002

OTHER PUBLICATIONS

D. Zhu et al., "A novel human immunoglobulin Fc gamma Fc epsilon bifunctional fusion protein inhibits Fc epsilon RI-mediated degranulation", Nat. Med. 8(5):5, pp. 518-521, (2002).
T. Yamada et al., <<Inhibition of interleukin-4-induced class switch recombination by a human immunoglobulin FC gamma-Fc epsilon chimeric protein, J. Biol. Chem. 278(35), pp. 32818-32824, (2003).
CL Kepley et al., "FcepsilonRI-FcgammaRII coaggregation inhibits IL-16 production from human Langerhans-like dendritic cells", Clin. Immunol. 108(2), pp. 89-94, (2003).
Lisa Chan Allen, et al., "Modifications to Fcγ-Fcε fusion protein alter its effectiveness in the inhibition of FcεRI-mediated functions", J Allergy Clinical Immunology, pp. 1-7 (2007).
James S. Huston, et al., "Protein engineering of antibody binding sites: Recovery of specific activity in an anti-digoxin single-chain Fv analogue produced in *Escherichia coli*", Proc. Natl. Acad. Sci. USA vol. 85, pp. 5879-5883, Aug. 1998.
Michael R. Van Scott, et al., "Systemic adminstration of an Fcγ-Fcε -fusion protein in house dust mite sensitive nonhuman primates", Clinical Immunology, vol. 128, pp. 340-348 (2008).

* cited by examiner

*Primary Examiner*—Michael Szperka
(74) *Attorney, Agent, or Firm*—Sughrue Mion, PLLC (57) ABSTRACT

This invention provides a fusion protein (FP4) and the code gene, expression method, and clinical application; its goal is to provide a fusion protein, the code gene, and the expression method as well as to take this fusion protein as the active constituent anti-allergic medicine. In addition, the invention provides the sequence of fusion protein attached on SEQ ID 2 and any derivation protein of the fusion protein (FP4) which includes adding or deleting several amino acids of SEQ ID 2 as well as increasing or deducing nuclear tides of SEQ ID 1. We designed to cross-link IgE active receptor and an IgG inhibitory receptor by endogens hinge without any extraneous chemical link. This invention fusion protein has function to block the IgE acceptor, moreover fragment of fusion protein has ability to specifically bind to a native IgG inhibitory receptor containing immunoreceptor tyrosine-based inhibitory motif, thereby inhibiting the IgE-driven mediator release from mast cells and basophils. It will play important role in the allergic disease treatment.

2 Claims, 7 Drawing Sheets

Figure 1, FP4 Molecular Structure

Figure 2, Flow Chart of FP4 Cloning

Figure 3,
Screening positive clones by restriction enzyme digestion

Figure 4, Flow analysis of FP4 binding ability to CHO cells

Figure 5, Flow analysis of FP4 binding ability to HMC-1 cells

Figure 6, FP4 protein inhibited histamine release in human basophils

Figure 7, FP4 blocked allergic reaction in the transgenic mice

FUSION PROTEIN FOR TREATMENT OF ALLERGIC DISEASES

FIELD OF THE INVENTION AND TECHNOLOGY

This invention is a fusion protein with its genetic code's expression method and application involved in the genetic engineering and the immunological fields, especially when this fusion protein act as the active ingredient of anti-allergic medicine.

BACKGROUND OF THE INVENTION

Allergenic disease is the sixth major cause to acute and chronic diseases. The disease has a strong genetic component and has a 30-60% chance of inheritability. Allergic rhinitis affects the eyes, nose and sinuses. It causes stuffy or runny nose, ears and throat postnasal, watery or itchy eyes, and bronchial tube irritation, also known as hay fever. Allergic dermatitis affects the skin, causing an itchy rash. It is also known as contact dermatitis. Asthma affects the lungs, causing shortness of breath or wheezing. Food allergies affect the stomach and other internal organs, and may also cause symptoms to the entire body. Urticaria is a condition resulting with hives on the skin. One type of allergic reaction that requires special attention is anaphylaxis, which is sudden, severe, and potentially fatal, with symptoms that can affect various areas of the body. The symptoms usually appear very quickly after exposure to the allergen and can include intense itching all over the body, full-body swelling, respiratory distress, and can even lead to life threatening shock. Approximately 10-15% of Chinese and around 20% of American population are affected by the allergic disease as well as other countries.

As of present, uses in treating the allergic disease the medicine mostly for the control clinical symptom, steroid hormone, the antihistamine medicine, medicine for reduces the hyperemia, and the bronchial tube relaxant; Recently American FDA has authorized in the clinical test anti-IgE monoclonal antibody. These medicines have the varying degree side effect. Research institutes, the universities and the pharmaceutical companies are seeking a new anti-allergic medicine.

The allergic reaction mechanism is: an immune system reaction to a typically harmless substance. The immune system is always working to fight off parasites, fungi, viruses and bacteria. However, sometimes the immune system will treat a harmless substance (called an allergen) as an unwanted invader and try to fight it. This overreaction of the body's immune system to a typically harmless substance is called an allergic reaction.

A hallmark of the allergic diathesis is the tendency to maintain a persistent IgE response after antigen (allergen) presentation. The initial exposure to antigens stimulates the production of specific IgE molecules, which bind to high-affinity Fc receptors on the surface of mast cells. Upon reexposure of antigens, the cross-linking of antigens and membrane-bound IgE molecules result in the release of vasoactive mediators, setting off subsequent clinical manifestation of sneezing, pruritus, and bronchospasm. Immunoglobulin receptors (also referred to as Fc receptors), are cell-surface receptors of mast cells, that bind to the constant region of immunoglobulins, and mediate various immunoglobulin functions other than antigen binding.

Fc receptors that bind with IgE molecules (a type of immunoglobulin) are found on many types of cells in the immune system. There are two different Fc receptors currently known for IgE, the multichain high-affinity receptor, FcεRI, and the low-affinity receptor, FcεRII. IgE molecules mediate its biological responses as an antibody through these Fc receptors. The high-affinity FcεRI receptor, expressed on the surface of mast cells, basophils, and Langerhans cells, belongs to the immunoglobulin gene superfamily, and has a tetrametric structure composed of an α-chain, a β-chain and two disulfide-linked γ-chains that are required for receptor expression and signal transduction. The α-chains of the receptor interact with the distal portion of the third constant domain of the IgE heavy chain. The specific region of the human IgE molecule involved in binding to the human FcεRI receptor have been identified as including six amino acids, Arg-408, Ser-411, Lys-415, Glu-452, Arg-465, and Met-469. The interaction is highly specific with a binding constant of about $10^{10}M^{-1}$.

The low-affinity FcεRII receptor, represented on the surface of inflammatory cells, such as eosinophils, leukocytes, B lymphocytes, and platelets, did not evolve from the immunoglobulin superfamily but has substantial homology with several groups of animals and is made up of a transmembrane chain with an intracytoplasmic $NH_2$ terminus. The low-affinity receptor, FcεRII (CD23), is currently known to have two forms, FcεRIIa and FcεRIIb, both of which have been cloned and sequenced. The two forms differ only in the N-terminal cytoplasmic region, with the extracellular domains being identical. FcεRIIa is normally expressed on B cells, while FcεRIIb is expressed on T cells, B cells, monocytes and eosinophils upon induction by the cytokine IL-4.

Through the high-affinity FcεRI receptor, IgE plays key roles in an array of acute and chronic allergic reactions, including asthma, allergic rhinitis, atopic dermatitis, severe food allergies, chronic urticaria and angioedema, as well as the serious physiological condition of anaphylactic shock. The binding of a multivalent antigen to an antigen-specific IgE molecule, which is specifically bound to a FcεRI receptor on the surface of a mast cell or basophil, stimulates a complex series of signaling events that culminate in the release of host vasoactive and proinflammatory mediators that contributes to both acute and late-phase allergic responses.

The function of the low-affinity FcεRII receptor (also referred to as CD23), found on the surface of B lymphocytes, is less well-established than that of the FcεRI receptor. FcεRII, in a polymeric state, binds to IgE molecules, and this binding may play a role in controlling the type (class) of antibody produced by B cells.

Three groups of Fcγ receptors that bind to the constant region of human IgG molecules have so far been identified on cell surfaces. They are, FcγRI (CD64), FcγRII (CD32), and FcγRIII (CD16), all of which belong to the immunoglobulin gene superfamily. The three Fcγ receptors have a large number of various isoforms.

In addition to the stimulatory FcεRI receptor, mast cells and basophils also co-express an immunoreceptor tyrosine-based inhibition motif (ITIM)-containing inhibitory low-affinity receptor, called the FcγRIIb receptor, which act to negatively regulate antibody functions. The FcγRIIb receptor belongs in the inhibitory receptor superfamily (IRS), which is a growing family of structurally and functionally similar inhibitory receptors that negatively regulate immunoreceptor tyrosine-based activation motif (ITAM)-containing immune receptors and a diverse array of other cellular responses. Coaggregation of an IRS member (such as FcγRIIb receptor) with an activating receptor (such as FcεRI receptor) leads to phosphorylation of the characteristic ITIM tyrosine and subsequent recruitment of the SH2 domain-containing protein tyrosine phosphatases SHP-1 and SHP-2, and the SH2 domain-containing phospholipases, SHIP and SHIP2. Possible outcomes of the coaggregation include inhibition of cellular activation, as demonstrated by the coaggregation of FcγRIIb and B-cell receptors, T-cell receptors, and activating receptors, such as FcεRI and cytokine. A key contributor to asthma, allergic rhinitis and severe food reactions is the induced IgE-driven mediators released from mast cells and basophils. The cross-linking of a mast cell or basophil FcεRI receptor with a multivalent antigen, activates tyrosine phosphorylation of immunoreceptor tyrosine-based activation motifs (ITAMs) in the β- and γ-FcεRI subunit cytoplasmic tails, thereby initiating downstream signaling through Syk. Mast cells and basophils also express the FcγRIIb receptor, which contains a single conserved immunoreceptor tyrosine-based inhibition motif (ITIM) within its cytoplasmic tail. Studies indicate that the aggregating of FcγRIIb to FcεRI leads to rapid tyrosine phosphorylation of the FcγRIIb ITIM tyrosine by FcεRI-associated Lyn and inhibition of FcεRI signaling. This hypothesis has been supported in experiments using human Ig Fcγ-Fcε fusion proteins that directly cross-link the FcεRI and FcγRIIb receptors on human basophils.

Invention Publication

The goal of this invention is to provide a genetic gene and its encoding fusion protein; this fusion protein has an anti-allergic activity.

Figure 1:
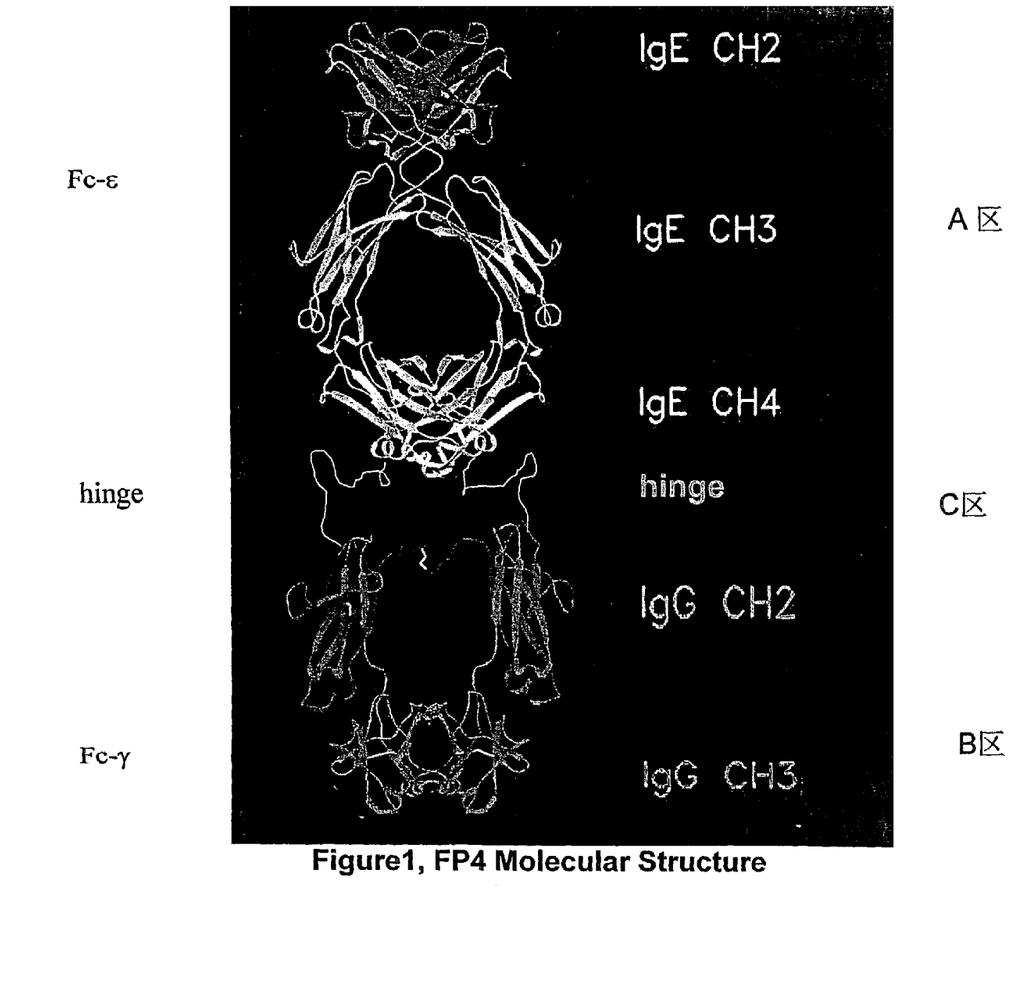
FIG. 1: FP4 Molecular Structure
FIG. 2 FP4 Cloning Flow Chart

The fusion protein used in this invention, named FP4, which is a function protein sequenced amino acid as SEQ ID No 2, or any derivation protein from sequencing of SEQ ID 2.; or any substitution, by decreasing or increasing several amino acid of SEQ ID No 2 amino acid sequence. The FP4 fusion protein from amino acid sequence of SEQ ID 2 contains 554 amino acids (see FIG. 1). FP4 structure is composed of three parts: A area (Fcε) (1-300$^{th}$ amino acids from N-end), B area (Fcγ) (318-554$^{th}$ amino acids from N-end) and C area (hinge) (301-317$^{th}$ amino acids from N-end). Among them, the A area originates from human immunoglobulin IgE and is the ligand of IgE receptor FcεRI; the B area originates from human immunoglobulin IgG and has the ligand of IgG receptor FcγRII; the C area originates from human immunoglobulin IgG, a twisting structure.

The fusion protein, FP4, has the following sequences:
1.) Figure of SEQ ID No. 1: DNA sequence;
2.) Figure of SEQ ID No. 2: Amino acid sequences.
3.) Any DNA sequence has more than 95% homology, and also encodes the same function protein sequence.

Sequence 1's DNA sequence is composed of 1665 base pair; the reading frame is from the 1st base pair to the 1665$^{th}$ base pair starting with the 5' end.

Anything including the genes and expression cell lines is under the patent protection of this invention. The primers used to amplify the encoding genes are also included in protection of this invention.

Expansion in any fragment of FP4 is also covered in the extent of this patent's protection.

The second goal of this invention is to introduce a method of expression for fusion protein FP4.

The method of FP4 expression introduced in this invention is to transfect the FP4 gene into SP 2/0 cell in order to get the positive clones which express the fusion protein FP4.

The expression vector is constructed by using regular methods to clone FP4 gene into pSecTag vector.

The third goal of this invention is to present an anti-allergic medicine whose active ingredient is fusion protein FP4.

If necessary, one can add one or multiple carriers to the medicine mentioned above. These carriers include pharmaceutical convention diluents, the excipient, the auxiliaries, the bond, the wetting agent, the disintegration medicinal preparation, the absorption promoter, the active surface agent, the absorption carrier, and the lubricant. When needed, one may also add flavoring agents and sweetening agents among other items.

Medicine from this invention can be used with an intravenous injection, a hypodermic injection, applied to the skin directly among other methods. It also can be used as a nasal spray and as a throat, mouth, skin, or membrane inhaler. In addition, this medicine can be applied as a nasal aqueous suspension, eye drops, or ear drops. Furthermore, it can be used as a rectal gel, pill, powder, ball pill, capsule, solution, oil cream, cream, and various other forms. The methods mentioned above can be pharmaceutically prepared with conventional methods to determine the correct dosages.

All the medicines mentioned above generally have a dosage of 0.01-lug/kg/day and the treatment course generally lasts 10 to 20 days.

BEST WAY TO CARRY OUT THE IMPLEMENTATION PROCESS

Implementation 1: fusion protein FP4's expression.

Figure 2:
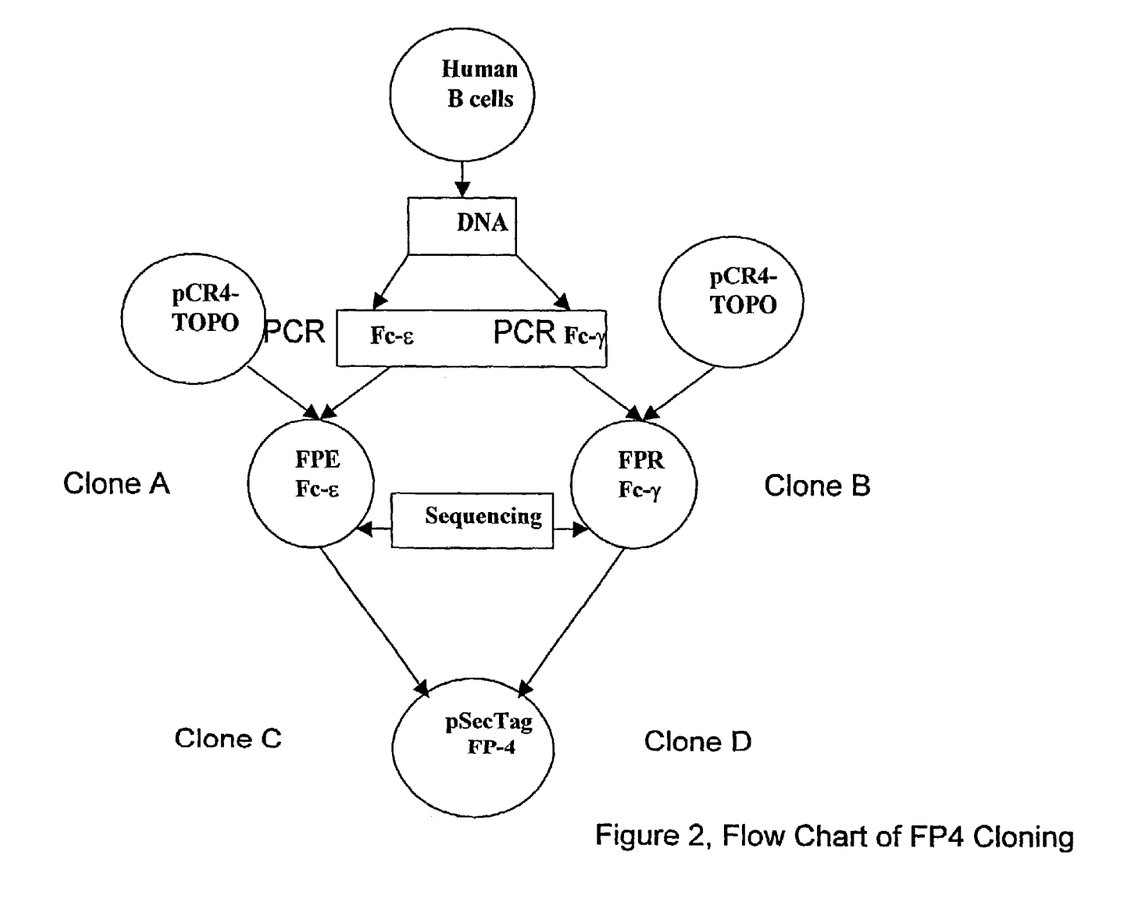

As figure 2 illustrates, fusion protein FP4's expression process includes the following steps the exact translation of the term), purify the B lymphocyte from human's circumference blood, specifically: Carries on the regular procedure with instruction below: separate (not sure extract genome DNA, direct things with the specificity:

P1(Fc$_ε$):5'-GTGGCCCAGCCGGCCTTCACCCCGC-CCACCGTGAAG-3'(SEQ ID NO: 3);
P2(Fc$_ε$):5'-GTGGATCCTTTACCGGGATTTACAGA-CAC-3'(SEQ ID NO: 4);
P3(Fc$_γ$):5'-GGGGATCCGAGCCCAAATCTTGTGAC-3'(SEQ ID NO: 5);
P4(Fc$_γ$):5'-GTGCGGCCGCTCATTTACCCGGAGA-CAGGGAGAG-3'(SEQ ID NO: 6)

Figure 3A:
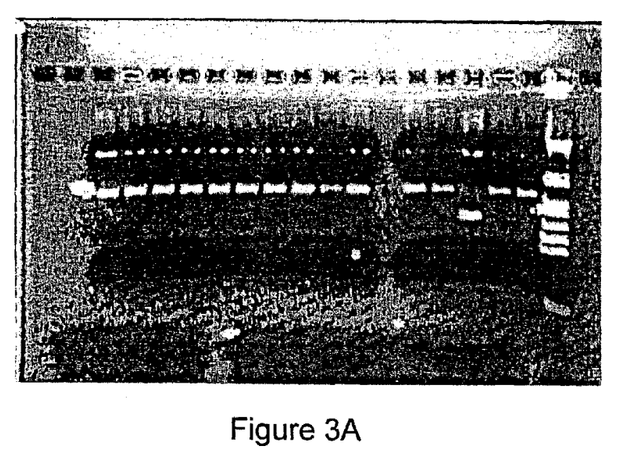
FIG. 3A: Electrophoresis Analysis of Fcε PCR products
Figure 3B:
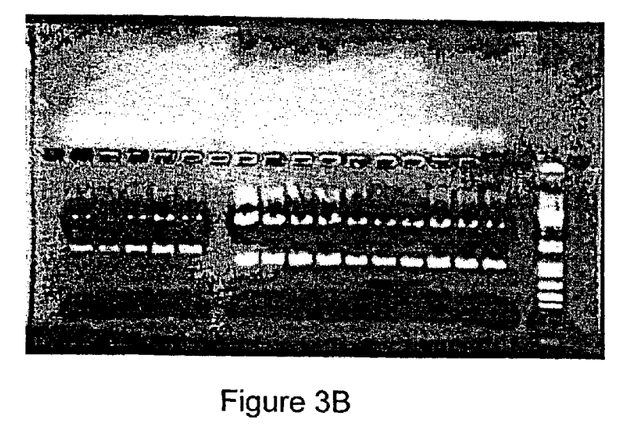
FIG. 3B: Electrophoresis Analysis of Fcγ PCR products.

We amplified Fcε and Fcγ genes by using Polymerase Chain Reaction, PCR products of Fcε and Fcγ were run on 1% agarose gel electrophoresis, the result was shown in FIG. 3, Fcε DNA PCR product is 1155 bp; Fcγ DNA PCR product is 928 bp. The PCR products were directly clone into pCR4-TOPO Vector (INVITROGEN, CA). After ligation, we obtained FPEFc-ε and FPGFc-γ and did the nucleotide sequence analysis. After confirming the nucleotide sequences correct, Fcε gene was cut by SfiI-BamHI (NEW ENGLAND BIOLABS); Fcγ gene was cut by BamHI-NotI. At mean time pSecTag expression vector (INVITROGEN,CA) was cut by Sfi I-Not I and then ligated with Fcε and Fcγ into pSec-TagFP4. We confirmed the insertion sequence is the same as that in FIG. 1. The pSecTagFP4 vector was transfected by electroporation into mouse myeloma SP2/0 cell. After selection with ZEOCIN, the positive clones were screened by ELISA (coating the plate with the mouse anti-human IgE, adding the supernatants of clones, then adding goat anti-human IgE conjugated with AP). We obtained the positive clones highly expressing FP4 protein.

We cultured the positive clones by using 10% FBS RPMI 1640 medium (Invitrogen, CA) in 37° C. 5% $CO_2$ for 15 days. We collected the supernatants by 2000 rpm centrifuge and purified the FP4 protein by using anti-human IgE affinity column (coupling mouse anti-human IgE to CNBr-activated Sepharose 4B(PHARMACIA).

Implementation 2:FP4 and FcεRI Receptor Binding Experiment

Figure 4:
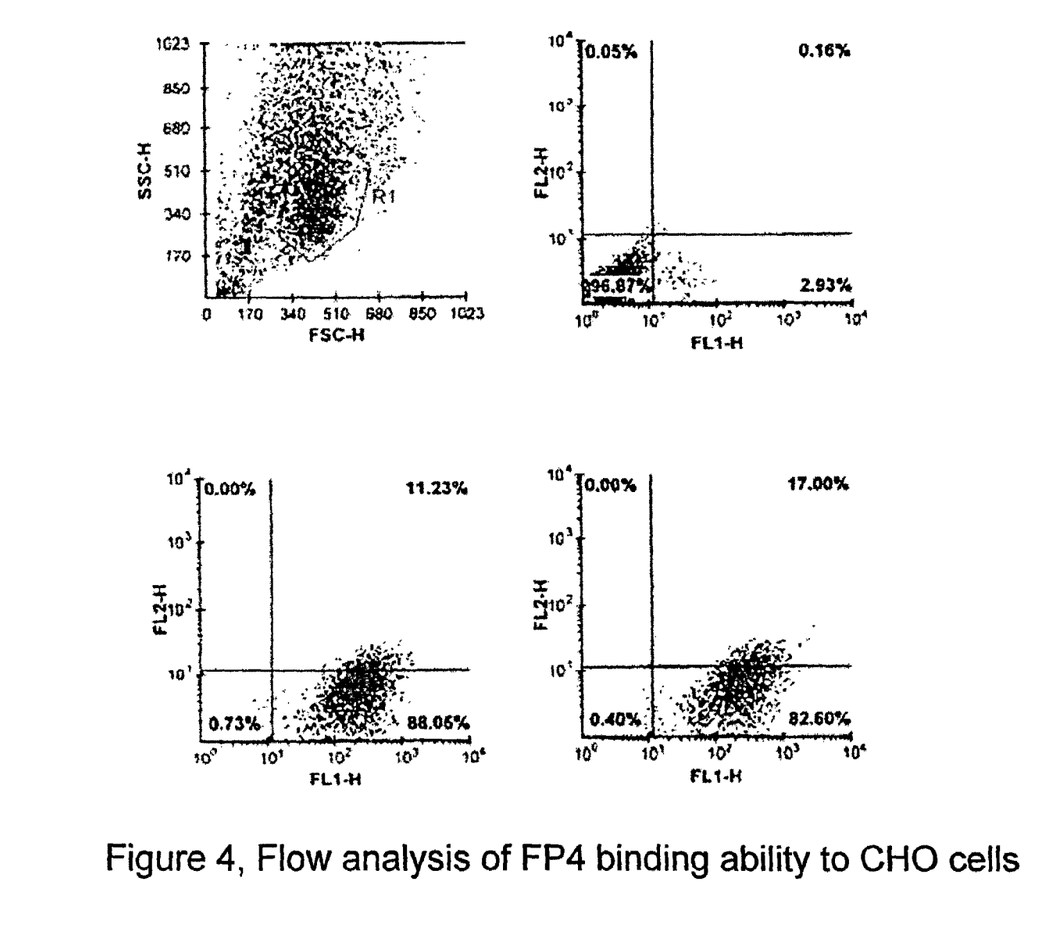
FIG. 4: Flow Analysis of FP4 binding ability to FcεRI receptor.

Incubated $1\times10^6$ CHO3D10 cells with 5 μg of Purified FP4 at 4° C. 1 hour, then added 5 ul of FITC labeled anti-human IgE (CALTAG,CA), analyzed with flow cytometry. The result was shown in FIG. 4. FP4 protein binds FcεRI receptor, presenting FITC positive of CHO3D10; In FIG. 4, SSC-H is in the cytoplasmic granularity, FSC-H is the cell size, FL2-H is PE, FL 1-H is FITC.

Implementation 3: FP4 and FcγRII Receptor Binding Experiment

Figure 5:
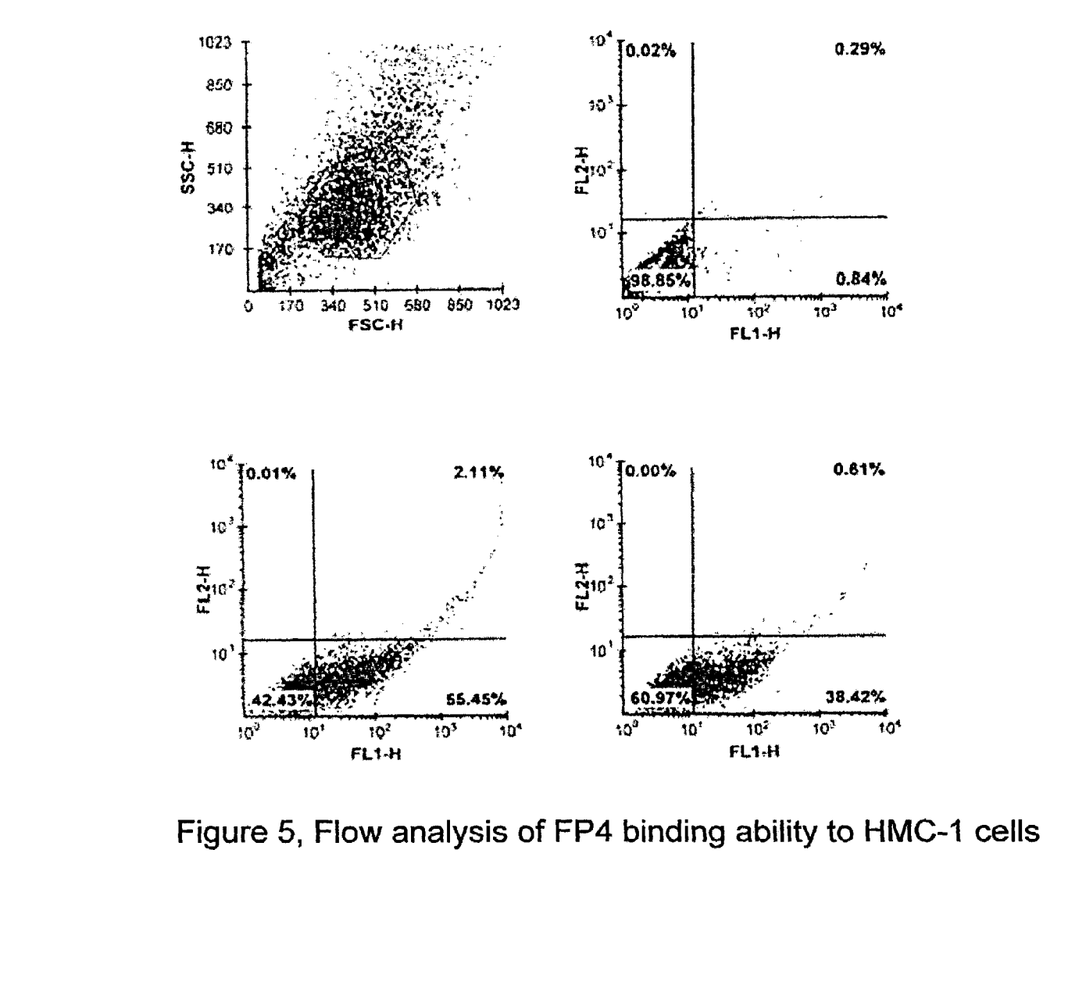
FIG. 5: Flow Analysis of FP4 binding ability to FcγRII receptor

Incubated $1\times10^6$ HMC-1 cell and 5 μg of Purifies FP4 protein at 4° C. 1 hour, added 5 μl of FITC labeled anti-human IgG (CALTAG, CA), analyzed with flow cytometry. The result shown that FP4 protein binds to FcγRII receptor, the HMC-1 cell presenting FITC positive(see FIG. 5), SSC-H is the cell granularity, FSC-H is the cell size, FL2-H is PE, FL1-H is FITC.

Implementation 4: FP4 Protein in vitro Function Experiment

Figure 6:
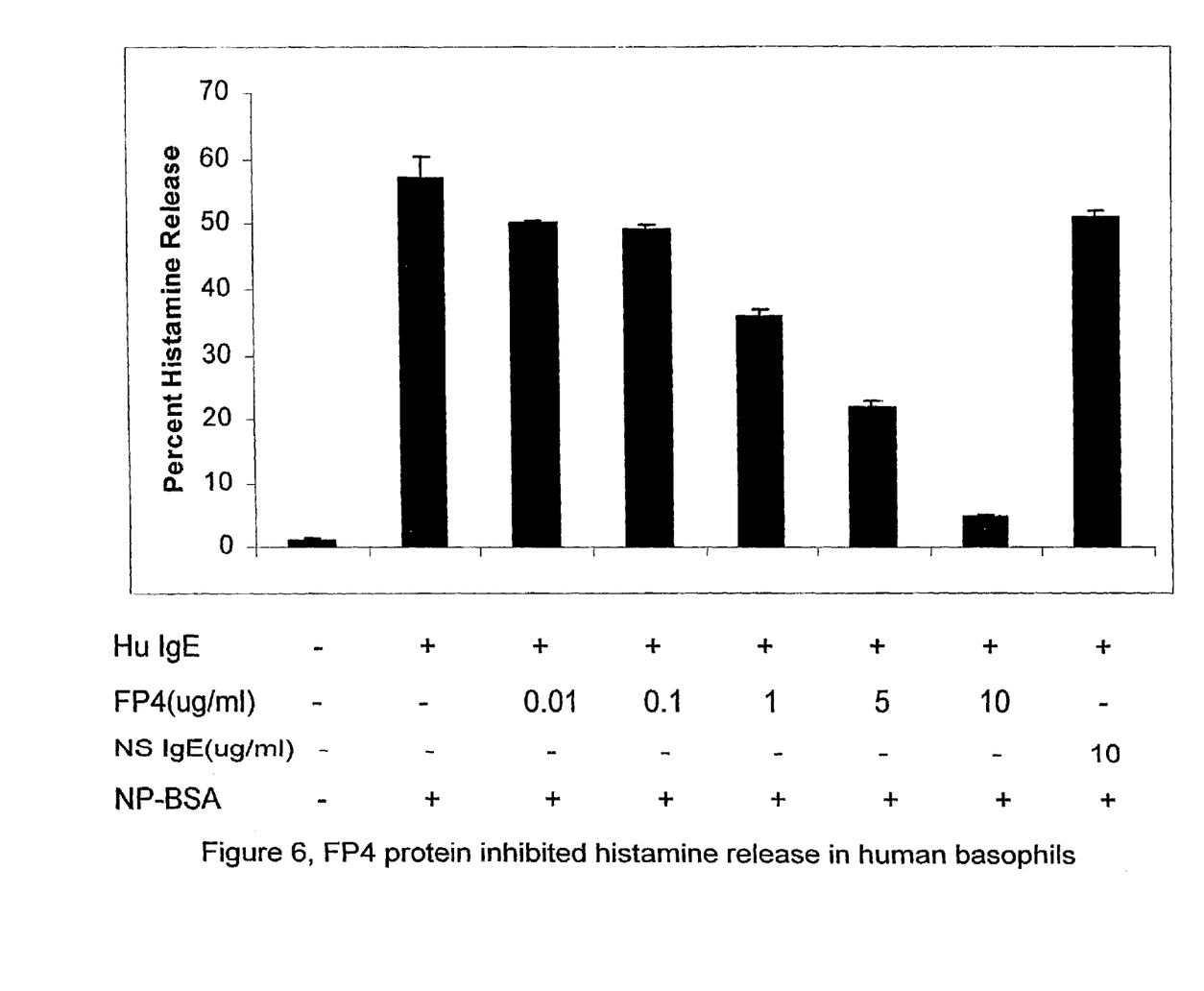
FIG. 6: FP4 protein inhibited histamine release in human basophils
Figure 7:
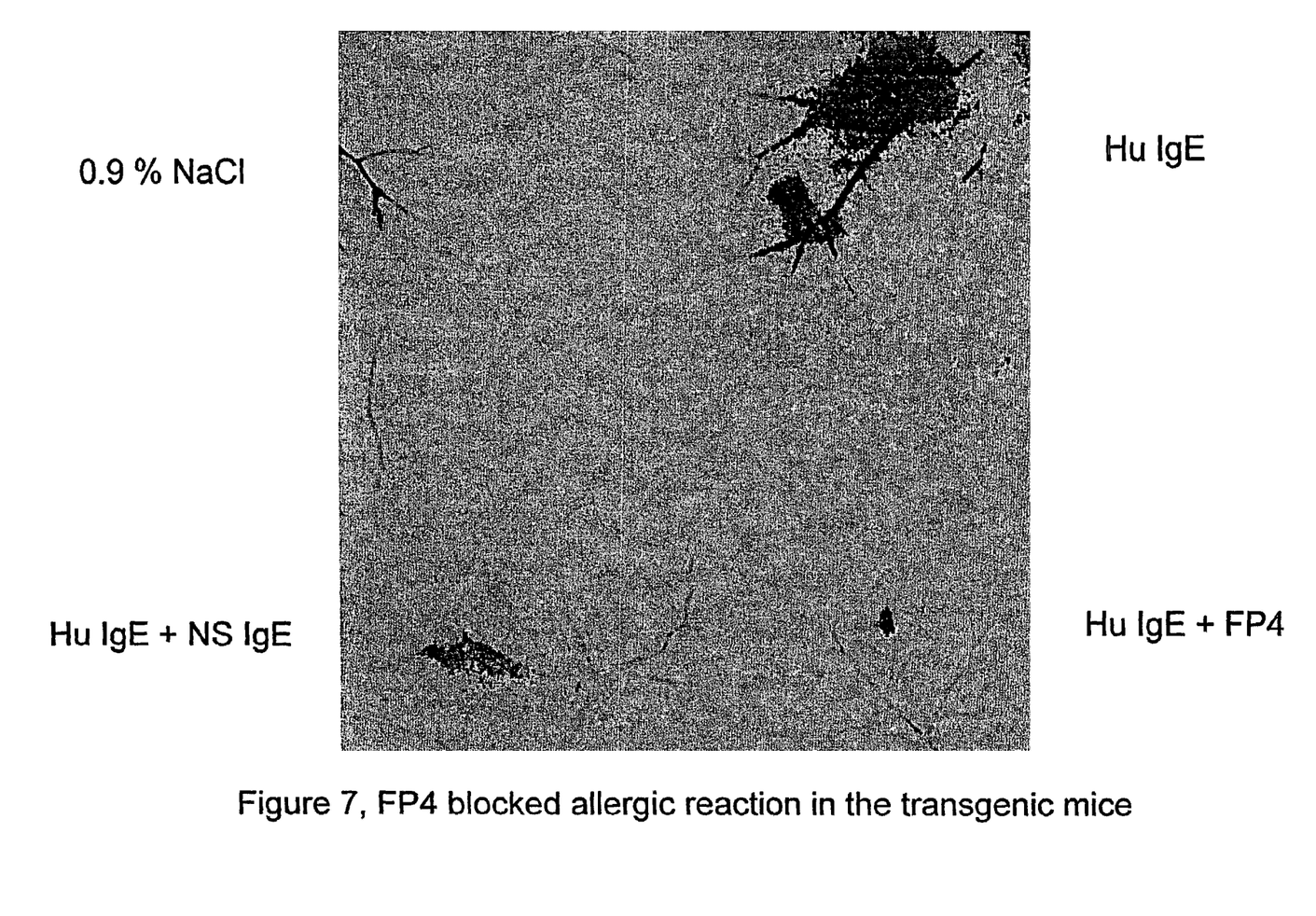
FIG. 7: FP4 fusion protein blocked allergic reaction in the transgenic mice.

We separated and purified human basophil from human peripheral blood. The purified basophils($1\times10^6$) were incubated with 1-10 μg specific human anti-NP-IgE (SEROTECH) at 37° C. for 2 hours, and then added 2 μg NP-BSA, the histamine release was measured by ELISA. The results showed that FP4 protein significantly inhibited histamine release in human basophils in dose-dependent fashion (see FIG. 6). Hu IgE stands for human IgE, NS IgE stands non-specific human IgE, NP-BSA stands for allergen, +addition, −non addition.

Implementation 5:FP4 Protein in vivo Function Experiment

The human FcεRIα chain transgenic mouse (from University of California, San Diego) was injected intradermally with human anti-NP-IgE (SEROTECH), 4 hour later i.v. challenging 100 μg of NP-BSA plus 1% Evans (Sigma) blue dye. If allergic reaction occurs, the local skin color turns to blue because of the leakage of dye from blood vessel. When we added the same amount of fusion protein (FP4), then allergic reaction was completely blocked, the local skin color not presenting blue (see FIG. 6). This experimental result further proved the FP4 protein in vivo inhibited allergic reaction.

INDUSTRIAL APPLICATION

In this invention, fusion protein FP4's ingredients originate from human immunoglobulin. Therefore, this protein enters the human body as a medicine; it does not have any antigens (foreign body protein immunity source). Fusion protein FP4 area C (hinge) obtains characteristics such as being nimble, easily rotated, and able to connect FcεRI and FcγRII together, thus stimulating the cell to prohibit signal sending, which then prohibits cells from releasing various active biological particles and prevent allergic reactions from occurring. All these results from the body of the experiment prove that the fusion protein FP4 can effectively connect adipose cell or Fc_RI on the surface of basophil granular cell with Fc_RII, in order to prevent allergic reaction. Fusion protein FP4 from this invention not only obtains IgE monoclonal antibody to block the function of IgE acceptor, but more importantly it starts an allergic reaction inside the cell's signal transduction pathway by suppressing it. (starting allergic reaction more importantly in the cell the signal conduction system suppression system) Furthermore, it strengthens the suppression of the cell's allergic reaction, which will play a vital role in its allergic disease treatment.

```
Foreword tabulation (SEQ ID NO 1)

<160> 2

<210> 1

<211> 1665

<212> DNA

<213> Artificial sequence

<220>

<223>

<400> 1 ttcacccgc  ccaccgtgaa  gatcttacag  tcgtcctgcg  acggcggcgg  gcacttcccc    60
ccgaccatcc  agctcctgtg  cctcgtctct  gggtacaccc  cagggactat  caacatcacc   120
tggctggagg  acgggcaggt  catggacgtg  gacttgtcca  ccgcctctac  cacgcaggag   180
ggtgagctgg  cctccacaca  aagcgagctc  accctcagcc  agaagcactg  gctgtcagac   240
cgcacctaca  cctgccaggt  cacctatcaa  ggtcacacct  ttgaggacag  caccaagaag   300
tgtgcagatt  ccaacccgag  aggggtgagc  gcctacctaa  gccggcccag  cccgttcgac   360
ctgttcatcc  gcaagtcgcc  cacgatcacc  tgtctggtgg  tggacctggc  acccagcaag   420
```

```
gggaccgtga acctgacctg gtcccgggcc agtgggaagc ctgtgaacca ctccaccaga      480
aaggaggaga agcagcgcaa tggcacgtta accgtcacgt ccaccctgcc ggtgggcacc      540
cgagactgga tcgaggggga gacctaccag tgcagggtga cccacccccca cctgcccagg     600 gccctcatgc ggtccacgac caagaccagc ggcccgcgtg ctgccccgga agtctatgcg      660
tttgcgacgc cggagtggcc ggggagccgg acaagcgca ccctcgcctg cctgatccag       720
aacttcatgc tgaggacat ctcggtgcag tggctgcaca acgaggtgca gctcccggac       780
gcccggcaca gcacgacgca gccccgcaag accaagggct ccggcttctt cgtcttcagc      840
cgtctagagg tgaccagggc cgaatgggag cagaaagatg agttcatctg ccgtgcagtc      900
catgaggcag ctagcccctc acagaccgtc agcgagcgg tgtctgtaaa tcccggtaaa       960
ggatccgagc ccaaatcttg tgacaaaact cacacatgcc accgtgccc agcacctgaa       1020 ctcctggggg gaccgtcagt cttcctcttc ccccaaaac ccaaggacac cctcatgatc       1080
tcccggaccc ctgaggtcac atgcgtggtg gtggacgtga gccacgaaga ccctgaggtc      1140
aagttcaact ggtacgtgga cggcgtggag gtgcataatg ccaagacaaa gccgcgggag      1200
gagcagtaca acagcacgta ccgggtggtc agcgtcctca ccgtcctgca ccaggactgg      1260
ctgaatggca aggagtacaa gtgcaaggtc tccaacaaag ccctcccagc ccccatcgag      1320
aaaaccatct ccaaagccaa agggcagccc cgagaaccac aggtgtacac cctgccccca      1380
tcccgggatg agctgaccaa gaaccaggtc agcctgacct gcctggtcaa aggcttctat      1440
cccagcgaca tcgccgtgga gtgggagagc aatgggcagc cggagaacaa ctacaagacc      1500
acgcctcccg tgctggactc cgacggctcc ttcttcctct acagcaagct caccgtggac      1560
aagagcaggt ggcagcaggg gaacgtcttc tcatgctccg tgatgcatga ggctctgcac      1620
aaccactaca cgcagaagag cctctccctg tctccgggta aatga                     1665
```

SEQ ID NO 2

<210> 2

<211> 554

<212> PRT

<213> Artificial sequence

<220>

<223>

<400> 2

```
Phe Thr Pro Pro Thr Val Lys Ile Leu Gln Ser Ser Cys Asp Gly
 1               5                  10                  15
Gly Gly His Phe Pro Pro Thr Ile Gln Leu Leu Cys Leu Val Ser
                20                  25                  30
Gly Tyr Thr Pro Gly Thr Ile Asn Ile Thr Trp Leu Glu Asp Gly
                35                  40                  45
Gln Val Met Asp Val Asp Leu Ser Thr Ala Ser Thr Thr Gln Glu
                50                  55                  60
Gly Glu Leu Ala Ser Thr Gln Ser Glu Leu Thr Leu Ser Gln Lys
                65                  70                  75
His Trp Leu Ser Asp Arg Thr Tyr Thr Cys Gln Val Thr Tyr Gln
                80                  85                  90
Gly His Thr Phe Glu Asp Ser Thr Lys Lys Cys Ala Asp Ser Asn
                95                  100                 105
Pro Arg Gly Val Ser Ala Tyr Leu Ser Arg Pro Ser Pro Phe Asp
```

-continued

```
                110                 115                 120
Leu Phe Ile Arg Lys Ser Pro Thr Ile Thr Cys Leu Val Val Asp 125                 130                 135
Leu Ala Pro Ser Lys Gly Thr Val Asn Leu Thr Trp Ser Arg Ala 140                 145                 150
Ser Gly Lys Pro Val Asn His Ser Thr Arg Lys Glu Glu Lys Gln 155                 160                 165
Arg Asn Gly Thr Leu Thr Val Thr Ser Thr Leu Pro Val Gly Thr 170                 175                 180
Arg Asp Trp Ile Glu Gly Glu Thr Tyr Gln Cys Arg Val Thr His 185                 190                 195
Pro His Leu Pro Arg Ala Leu Met Arg Ser Thr Thr Lys Thr Ser 200                 205                 210
Gly Pro Arg Ala Ala Pro Glu Val Tyr Ala Phe Ala Thr Pro Glu 215                 220                 225
Trp Pro Gly Ser Arg Asp Lys Arg Thr Leu Ala Cys Leu Ile Gln 230                 235                 240
Asn Phe Met Pro Glu Asp Ile Ser Val Gln Trp Leu His Asn Glu 245                 250                 255
Val Gln Leu Pro Asp Ala Arg His Ser Thr Thr Gln Pro Arg Lys 260                 265                 270
Thr Lys Gly Ser Gly Phe Phe Val Phe Ser Arg Leu Glu Val Thr 275                 280                 285
Arg Ala Glu Trp Glu Gln Lys Asp Glu Phe Ile Cys Arg Ala Val 290                 295                 300
His Glu Ala Ala Ser Pro Ser Gln Thr Val Gln Arg Ala Val Ser 305                 310                 315
Val Asn Pro Gly Lys Gly Ser Glu Pro Lys Ser Cys Asp Lys Thr 320                 325                 330
His Thr Cys Pro Pro Cys Pro Ala Pro Glu Leu Leu Gly Gly Pro 335                 340                 345
Ser Val Pro Leu Pro Pro Pro Lys Pro Lys Asp Thr Leu Met Ile 350                 355                 360
Ser Arg Thr Pro Glu Val Thr Cys Val Val Val Asp Val Ser His 365                 370                 375
Glu Asp Pro Glu Val Lys Pro Asn Trp Tyr Val Asp Gly Val Glu 380                 385                 390
Val His Asn Ala Lys Thr Lys Pro Arg Glu Glu Gln Tyr Asn Ser 395                 400                 405
Thr Tyr Arg Val Val Ser Val Leu Thr Val Leu His Gln Asp Trp 410                 415                 420
Leu Asn Gly Lys Glu Tyr Lys Cys Lys Val Ser Asn Lys Ala Leu 425                 430                 435
Pro Ala Pro Ile Glu Lys Thr Ile Set Lys Ala Lys Gly Gln Pro 440                 445                 450
Arg Glu Pro Gln Val Tyr Thr Leu Pro Pro Ser Arg Asp Glu Leu 455                 460                 465
Thr Lys Asn Gln Val Ser Leu Thr Cys Leu Val Lys Gly Pro Tyr 470                 475                 480
Pro Ser Asp Ile Ala Val Glu Trp Glu Ser Asn Gly Gln Pro Glu 485                 490                 495
Asn Asn Tyr Lys Thr Thr Pro Pro Val Leu Asp Ser Asp Gly Ser 500                 505                 510
```

-continued

```
Pro Pro Leu Tyr Ser Lys Leu Thr Val Asp Lys Ser Arg Trp Gln
            515                 520                 525
Gln Gly Asn Val Pro Ser Cys Ser Val Met His Glu Ala Leu His
            530                 535                 540
Asn His Tyr Thr Gln Lys Ser Leu Ser Leu Ser Pro Gly Lys
            545                 550             554
```

SEQUENCE LISTING

<160> NUMBER OF SEQ ID NOS: 6

<210> SEQ ID NO 1
<211> LENGTH: 1665
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 1

| | | | | | | |
|---|---|---|---|---|---|---|
| ttcaccccgc | ccaccgtgaa | gatcttacag | tcgtcctgcg | acggcggcgg | gcacttcccc | 60 |
| ccgaccatcc | agctcctgtg | cctcgtctct | gggtacaccc | cagggactat | caacatcacc | 120 |
| tggctggagg | acgggcaggt | catggacgtg | gacttgtcca | ccgcctctac | cacgcaggag | 180 |
| ggtgagctgg | cctccacaca | aagcgagctc | accctcagcc | agaagcactg | gctgtcagac | 240 |
| cgcacctaca | cctgccaggt | cacctatcaa | ggtcacacct | tgaggacag | caccaagaag | 300 |
| tgtgcagatt | ccaacccgag | aggggtgagc | gcctacctaa | gccggcccag | cccgttcgac | 360 |
| ctgttcatcc | gcaagtcgcc | cacgatcacc | tgtctggtgg | tggacctggc | acccagcaag | 420 |
| gggaccgtga | acctgacctg | gtcccgggcc | agtgggaagc | tgtgaacca | ctccaccaga | 480 |
| aaggaggaga | agcagcgcaa | tggcacgtta | accgtcacgt | ccaccctgcc | ggtgggcacc | 540 |
| cgagactgga | tcaggggga | gacctaccag | tgcagggtga | cccacccca | cctgcccagg | 600 |
| gccctcatgc | ggtccacgac | caagaccagc | ggcccgcgtg | ctgccccgga | agtctatgcg | 660 |
| tttgcgacgc | cggagtggcc | ggggagccgg | acaagcgca | ccctcgcctg | cctgatccag | 720 |
| aacttcatgc | ctgaggacat | ctcggtgcag | tggctgcaca | acgaggtgca | gctcccggac | 780 |
| gcccggcaca | gcacgacgca | gccccgcaag | accagggct | ccggcttctt | cgtcttcagc | 840 |
| cgtctagagg | tgaccagggc | cgaatgggag | cagaaagatg | agttcatctg | ccgtgcagtc | 900 |
| catgaggcag | ctagccctc | acagaccgtc | agcgagcgg | tgtctgtaaa | tcccggtaaa | 960 |
| ggatccgagc | ccaaatcttg | tgacaaaact | cacacatgcc | caccgtgccc | agcacctgaa | 1020 |
| ctcctggggg | gaccgtcagt | cttcctcttc | cccccaaaac | ccaaggacac | cctcatgatc | 1080 |
| tcccggaccc | ctgaggtcac | atgcgtgtg | gtggacgtga | gccacgaaga | ccctgaggtc | 1140 |
| aagttcaact | ggtacgtgga | cggcgtggag | gtgcataatg | ccaagacaaa | gccgcgggag | 1200 |
| gagcagtaca | acagcacgta | ccgggtggtc | agcgtcctca | ccgtcctgca | ccaggactgg | 1260 |
| ctgaatggca | aggagtacaa | gtgcaaggtc | tccaacaaag | ccctcccagc | ccccatcgag | 1320 |
| aaaaccatct | ccaaagccaa | agggcagccc | cgagaaccac | aggtgtacac | cctgcccca | 1380 |
| tcccgggatg | agctgaccaa | gaaccaggtc | agcctgacct | gcctggtcaa | aggcttctat | 1440 |
| cccagcgaca | tcgccgtgga | gtgggagagc | aatgggcagc | cggagaacaa | ctacaagacc | 1500 |
| acgcctcccg | tgctggactc | cgacggctcc | ttcttcctct | acagcaagct | caccgtggac | 1560 |

-continued aagagcaggt ggcagcaggg gaacgtcttc tcatgctccg tgatgcatga ggctctgcac    1620
aaccactaca cgcagaagag cctctccctg tctccgggta aatga                    1665

<210> SEQ ID NO 2
<211> LENGTH: 554
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 2

Phe Thr Pro Pro Thr Val Lys Ile Leu Gln Ser Ser Cys Asp Gly Gly
1               5                   10                  15

Gly His Phe Pro Pro Thr Ile Gln Leu Leu Cys Leu Val Ser Gly Tyr
            20                  25                  30

Thr Pro Gly Thr Ile Asn Ile Thr Trp Leu Glu Asp Gly Gln Val Met
        35                  40                  45

Asp Val Asp Leu Ser Thr Ala Ser Thr Thr Gln Glu Gly Glu Leu Ala
    50                  55                  60

Ser Thr Gln Ser Glu Leu Thr Leu Ser Gln Lys His Trp Leu Ser Asp
65                  70                  75                  80

Arg Thr Tyr Thr Cys Gln Val Thr Tyr Gln Gly His Thr Phe Glu Asp
                85                  90                  95

Ser Thr Lys Lys Cys Ala Asp Ser Asn Pro Arg Gly Val Ser Ala Tyr
            100                 105                 110

Leu Ser Arg Pro Ser Pro Phe Asp Leu Phe Ile Arg Lys Ser Pro Thr
        115                 120                 125

Ile Thr Cys Leu Val Val Asp Leu Ala Pro Ser Lys Gly Thr Val Asn
    130                 135                 140

Leu Thr Trp Ser Arg Ala Ser Gly Lys Pro Val Asn His Ser Thr Arg
145                 150                 155                 160

Lys Glu Glu Lys Gln Arg Asn Gly Thr Leu Thr Val Thr Ser Thr Leu
                165                 170                 175

Pro Val Gly Thr Arg Asp Trp Ile Glu Gly Glu Thr Tyr Gln Cys Arg
            180                 185                 190

Val Thr His Pro His Leu Pro Arg Ala Leu Met Arg Ser Thr Thr Lys
        195                 200                 205

Thr Ser Gly Pro Arg Ala Ala Pro Glu Val Tyr Ala Phe Ala Thr Pro
    210                 215                 220

Glu Trp Pro Gly Ser Arg Asp Lys Arg Thr Leu Ala Cys Leu Ile Gln
225                 230                 235                 240

Asn Phe Met Pro Glu Asp Ile Ser Val Gln Trp Leu His Asn Glu Val
                245                 250                 255

Gln Leu Pro Asp Ala Arg His Ser Thr Thr Gln Pro Arg Lys Thr Lys
            260                 265                 270

Gly Ser Gly Phe Phe Val Phe Ser Arg Leu Glu Val Thr Arg Ala Glu
        275                 280                 285

Trp Glu Gln Lys Asp Glu Phe Ile Cys Arg Ala Val His Glu Ala Ala
    290                 295                 300

Ser Pro Ser Gln Thr Val Gln Arg Ala Val Ser Val Asn Pro Gly Lys
305                 310                 315                 320

Gly Ser Glu Pro Lys Ser Cys Asp Lys Thr His Thr Cys Pro Pro Cys
                325                 330                 335

-continued

```
Pro Ala Pro Glu Leu Leu Gly Gly Pro Ser Val Pro Leu Pro Pro Pro
        340                 345                 350

Lys Pro Lys Asp Thr Leu Met Ile Ser Arg Thr Pro Glu Val Thr Cys
    355                 360                 365

Val Val Val Asp Val Ser His Glu Asp Pro Glu Val Lys Pro Asn Trp
370                 375                 380

Tyr Val Asp Gly Val Glu Val His Asn Ala Lys Thr Lys Pro Arg Glu
385                 390                 395                 400

Glu Gln Tyr Asn Ser Thr Tyr Arg Val Val Ser Val Leu Thr Val Leu
            405                 410                 415

His Gln Asp Trp Leu Asn Gly Lys Glu Tyr Lys Cys Lys Val Ser Asn
        420                 425                 430

Lys Ala Leu Pro Ala Pro Ile Glu Lys Thr Ile Ser Lys Ala Lys Gly
    435                 440                 445

Gln Pro Arg Glu Pro Gln Val Tyr Thr Leu Pro Pro Ser Arg Asp Glu
450                 455                 460

Leu Thr Lys Asn Gln Val Ser Leu Thr Cys Leu Val Lys Gly Pro Tyr
465                 470                 475                 480

Pro Ser Asp Ile Ala Val Glu Trp Glu Ser Asn Gly Gln Pro Glu Asn
            485                 490                 495

Asn Tyr Lys Thr Thr Pro Pro Val Leu Asp Ser Asp Gly Ser Pro Pro
        500                 505                 510

Leu Tyr Ser Lys Leu Thr Val Asp Lys Ser Arg Trp Gln Gln Gly Asn
    515                 520                 525

Val Pro Ser Cys Ser Val Met His Glu Ala Leu His Asn His Tyr Thr
530                 535                 540

Gln Lys Ser Leu Ser Leu Ser Pro Gly Lys
545                 550

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtggcccagc cggccttcac cccgcccacc gtgaag                              36

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtggatcctt taccgggatt tacagacac                                      29

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
```

```
ggggatccga gcccaaatct tgtgac                                          26

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtgcggccgc tcatttaccc ggagacaggg agag                                 34
```

We claim:

1. A fusion protein comprising the amino acid sequence of SEQ ID NO: 2.

2. A composition comprising the fusion protein of claim 1 and a carrier.

* * * * *